US009990266B2

(12) United States Patent
Moffatt (10) Patent No.: US 9,990,266 B2
(45) Date of Patent: Jun. 5, 2018

(54) DATA RECORDER FOR FULL EVENT CAPTURE

(71) Applicant: Sikorsky Aircraft Corporation, Stratford, CT (US)

(72) Inventor: Ronald Moffatt, Rochester, NY (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 1196 days.

(21) Appl. No.: 14/140,713

(22) Filed: Dec. 26, 2013

(65) Prior Publication Data

US 2015/0186244 A1 Jul. 2, 2015

(51) Int. Cl.
*G06F 17/40* (2006.01)
*G06F 11/34* (2006.01)
*G01L 5/14* (2006.01)
*G01L 5/00* (2006.01)
*G11B 20/10* (2006.01)
*G01P 1/12* (2006.01)
*F41A 19/01* (2006.01)
*G01L 9/00* (2006.01)

(52) U.S. Cl.
CPC .......... *G06F 11/3476* (2013.01); *G01L 5/14* (2013.01); *A61B 2560/0242* (2013.01); *A61B 2562/0247* (2013.01); *F41A 19/01* (2013.01); *G01L 5/0052* (2013.01); *G01L 9/008* (2013.01); *G01P 1/127* (2013.01); *G11B 20/10527* (2013.01)

(58) Field of Classification Search
CPC .... A61B 2560/0242; A61B 2562/0247; F41A 19/01; G01L 5/0052; G01L 5/14; G01L 9/008; G01P 1/127; G06F 11/3476; G11B 20/10527
See application file for complete search history.

(56) References Cited

U.S. PATENT DOCUMENTS

| 3,778,059 | A | | 12/1973 | Rohrbaugh et al. |
| 5,453,710 | A | | 9/1995 | Gilbert et al. |
| 5,524,489 | A | * | 6/1996 | Twigg ..................... B60T 8/171 73/514.26 |
| 5,978,972 | A | | 11/1999 | Stewart et al. |
| 6,222,409 | B1 | | 4/2001 | Kieda et al. |

(Continued)

OTHER PUBLICATIONS

Analog Devices, "16-Bit, 250 kSPS PulSAR ADC in MSOP AD7694" Rev. A., 2005, 16 pages.

(Continued)

*Primary Examiner* — David M Gray
*Assistant Examiner* — Geoffrey T Evans
(74) *Attorney, Agent, or Firm* — Cantor Colburn LLP (57) ABSTRACT

Embodiments are directed to capturing data associated with an occurrence of an event via a battery-powered recorder, comprising: storing analog data in a delay circuit while a recording circuit is powered off, detecting, by a trigger circuit, the occurrence of the event while the recording circuit is powered off, powering-on the recording circuit based on the detection of the event, converting samples of analog data associated with the event provided by the delay circuit to a digital format while the recording circuit powers on, and storing the converted digital samples after the recording circuit has powered on, wherein a time delay associated with the delay circuit is greater than a time it takes for the recording circuit to power-on.

14 Claims, 5 Drawing Sheets

(56) References Cited

U.S. PATENT DOCUMENTS

| | | | | |
|---|---|---|---|---|
| 6,400,652 | B1* | 6/2002 | Goldberg | G11B 15/087 |
| | | | | 360/7 |
| 7,526,389 | B2 | 4/2009 | Greenwald et al. | |
| 7,992,421 | B2 | 8/2011 | Jeftic-Stojanovski et al. | |
| 8,316,691 | B2 | 11/2012 | Jeftic-Stojanovski et al. | |
| 8,322,188 | B2 | 12/2012 | Jeftic-Stojanovski et al. | |
| 8,400,636 | B2 | 3/2013 | Smith et al. | |
| 2002/0072838 | A1* | 6/2002 | McClellan | G01D 9/005 |
| | | | | 73/489 |

OTHER PUBLICATIONS

Analog Devices, "MT-090 Tutorial Sample-and-Hold Amplifiers", Rev.0, 2009, 21 pages.

Mercedes Casamayor, "How to Save Power in Battery Applications Using the Power-Down Mode in an ADC", Analog Dialogue, vol. 37, Sep. 2003, 4 pages.

Texas Instruments, "Quad Channel 16-Bit, 100-MSPS High-SNR ADC ADS5263", SLAS760C—May 2011—Revised Jan. 2013, 82 pages.

* cited by examiner

DATA RECORDER FOR FULL EVENT CAPTURE

STATEMENT REGARDING FEDERALLY SPONSORED RESEARCH OR DEVELOPMENT

This invention was made with Government support with the United States Army under Contract No. W81XH-10-C-0012. The Government has certain rights in this invention.

BACKGROUND

People can be exposed to pressure waves. For example, military, law enforcement, and construction personnel can be exposed to explosions, blasts, or similar events when performing their duties. Medical experts are looking to correlate long-term injury with recordable blast signatures.

Monitoring devices may be segregated into two classes: (1) those that detect the peak level of a pressure wave, and (2) those that record the entire pressure waveform.

Monitoring devices that monitor only the peak level (e.g., the first class described above) fail to provide a rich dataset needed for research and injury tracking purposes.

Monitoring devices that record the entire pressure waveform (e.g., the second class described above) are subject to poor battery life due to the power requirements associated with the data acquisition components included in such devices. The nature of blasts and similar events is that they tend to be unpredictable in terms of when they will occur. An example of such a circuit 300 is shown in FIG. 3A.

The circuit 300 includes a sensor 1. The circuit 300 includes a conditioning amplifier 2 coupled to the sensor 1.

Figure 3A:
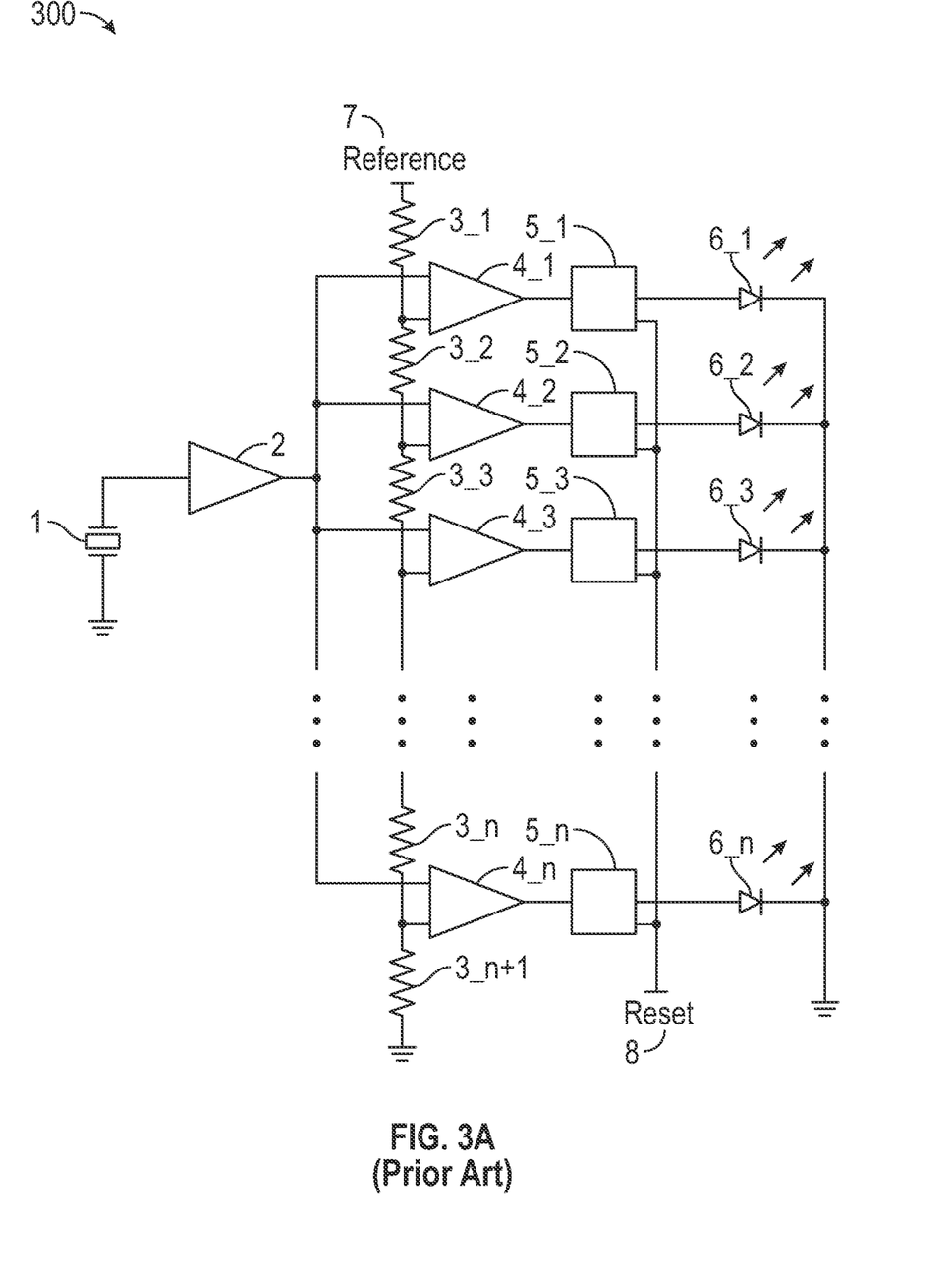
FIG. 3A illustrates a diagram of a circuit in accordance with the prior art.

The output of the conditioning amplifier 2 is coupled to a first input associated with each of a number 'n' of comparators 4, denoted in FIG. 3A as 4_1, 4_2, 4_3, ... 4_n. A second input of the comparators 4 is supplied with a reference voltage 7. Specifically, a reference applied to the comparators 4 corresponds to the reference voltage 7 divided by a resistor divider network composed of a number 'n' of resistors 3, denoted in FIG. 3A as resistors 3_1, 3_2, 3_3, ... 3_n, 3_n+1. The outputs of the comparators 4 are provided to a network of latches composed of a number 'n' of latches 5, denoted in FIG. 3A as latches 5_1, 5_2, 5_3, ... 5_n. The state of each of the latches 5 is reset by a reset signal 8. The output of each of the latches 5 is coupled to a network of indicators composed of a number 'n' of indicators 6, denoted in FIG. 3A as indicators 6_1, 6_2, 6_3, ... 6_n. The indicators 6 include light emitting diodes (LEDs).

The comparators 4 and latches 5 record only the maximum magnitude of an input wave. They record the time of occurrence of the blast event, but do not have the capability of recording the time characteristics (e.g., blast waveform).

BRIEF SUMMARY

An embodiment is directed to a method for capturing data associated with an occurrence of an event via a battery-powered recorder, comprising: storing analog data in a delay circuit while a recording circuit is powered off, detecting, by a trigger circuit, the occurrence of the event while the recording circuit is powered off, powering-on the recording circuit based on the detection of the event, converting samples of analog data associated with the event provided by the delay circuit to a digital format while the recording circuit powers on, and storing the converted digital samples after the recording circuit has powered on, wherein a time delay associated with the delay circuit is greater than a time it takes for the recording circuit to power-on.

An embodiment is directed to a system comprising: a trigger circuit to detect an occurrence of an event, a delay circuit to delay analog samples of data, and a recording circuit to store the delayed analog samples of data in a digital format when in a power-on state and to not store the delayed analog samples when in a power-off state, wherein a time delay associated with the delay circuit is greater than a time it takes for the recording circuit to power-on to the power-on state from the power-off state, and wherein the recording circuit is powered-on based on the detection of the occurrence of the event by the trigger circuit.

In addition to one or more of the features described above, or as an alternative, further embodiments could include a delay circuit configured as a multi tap track and hold circuit.

In addition to one or more of the features described above, or as an alternative, further embodiments could include a delay circuit that runs at a conversion rate of an analog to digital converter (ADC) included in a recording circuit.

In addition to one or more of the features described above, or as an alternative, further embodiments could include detecting an end of the event, and powering-off the recording circuit based on the detection of the end of the event.

In addition to one or more of the features described above, or as an alternative, further embodiments could include imposing a second time delay between the detection of an end of an event and a powering-off of a recording circuit a second time, wherein the second time delay is selected to enable digital samples associated with the event to be stored.

In addition to one or more of the features described above, or as an alternative, further embodiments could include a recording circuit comprising at least one analog to digital converter (ADC), wherein the at least one ADC is associated with a plurality of sensor circuits that provide analog data.

In addition to one or more of the features described above, or as an alternative, further embodiments could include synchronizing samples of analog data provided by sensor circuits.

In addition to one or more of the features described above, or as an alternative, further embodiments could include time-stamping the digital samples and storing the time-stamps with the digital samples in a non-volatile memory of a recording circuit.

In addition to one or more of the features described above, or as an alternative, further embodiments could include at least one sensor, wherein an output of the at least one sensor is coupled to an input of a trigger circuit.

In addition to one or more of the features described above, or as an alternative, further embodiments could include at least one sensor comprising at least one of: a magnetic coil, a piezoelectric sensor, and a thermocouple.

In addition to one or more of the features described above, or as an alternative, further embodiments could include an output of at least one sensor coupled to an input of a conditioning amplifier, wherein an output of the conditioning amplifier is coupled to an input of a trigger circuit.

In addition to one or more of the features described above, or as an alternative, further embodiments could include a trigger circuit comprising a comparator, wherein a reference is coupled to a first input of the comparator, and wherein the reference is selected to distinguish between the occurrence and the non-occurrence of an event.

In addition to one or more of the features described above, or as an alternative, further embodiments could include selection of a reference based on at least one of: a reference divider network and a programmable level setting device.

In addition to one or more of the features described above, or as an alternative, further embodiments could include selection of a reference based on an application associated with an event.

In addition to one or more of the features described above, or as an alternative, further embodiments could include a battery which powers a recording circuit.

In addition to one or more of the features described above, or as an alternative, further embodiments could include at least one of an indicator and a communication port configured to convey a status regarding at least one of an event, data, and digital samples.

In addition to one or more of the features described above, or as an alternative, further embodiments could include a battery which powers a recording circuit, and at least one of an indicator and a communication port configured to provide an indication that the battery is charged to an amount that is less than a threshold.

In addition to one or more of the features described above, or as an alternative, further embodiments could include a recording circuit that is configured to be powered-off after a second time delay based on a detection of an end of an occurrence of an event by a trigger circuit.

In addition to one or more of the features described above, or as an alternative, further embodiments could include a delay circuit comprising an analog input port, an analog output port coupled to an input of a recording circuit, hold capacitors to hold analog samples from the analog input port, a plurality of input switches selectively connecting the analog input port to the hold capacitors, a plurality of output switches selectively connecting the analog output port to the hold capacitors, and an address generator configured to control the plurality of input switches coupling the hold capacitors to the input analog port and the plurality of output switches coupling the hold capacitors and the output analog port, wherein the address generator connects the oldest analog sample present in the delay circuit to the output analog port.

Additional embodiments are described below.

BRIEF DESCRIPTION OF THE DRAWINGS

The present disclosure is illustrated by way of example and not limited in the accompanying figures in which like reference numerals indicate similar elements.

DETAILED DESCRIPTION

It is noted that various connections are set forth between elements in the following description and in the drawings (the contents of which are included in this disclosure by way of reference). It is noted that these connections in general and, unless specified otherwise, may be direct or indirect and that this specification is not intended to be limiting in this respect. In this respect, a coupling between entities may refer to either a direct or an indirect connection.

Exemplary embodiments of apparatuses, systems, and methods are described for enhancing the operational life (e.g., the operational battery life) of a monitor of explosive blast pressure waves. By extending the battery life, the probability that a monitor will detect and capture data regarding a pressure wave may be increased relative to conventional monitors. Moreover, by extending the battery life, a reduction in term of error prone field maintenance requirements may be realized.

Figure 1:
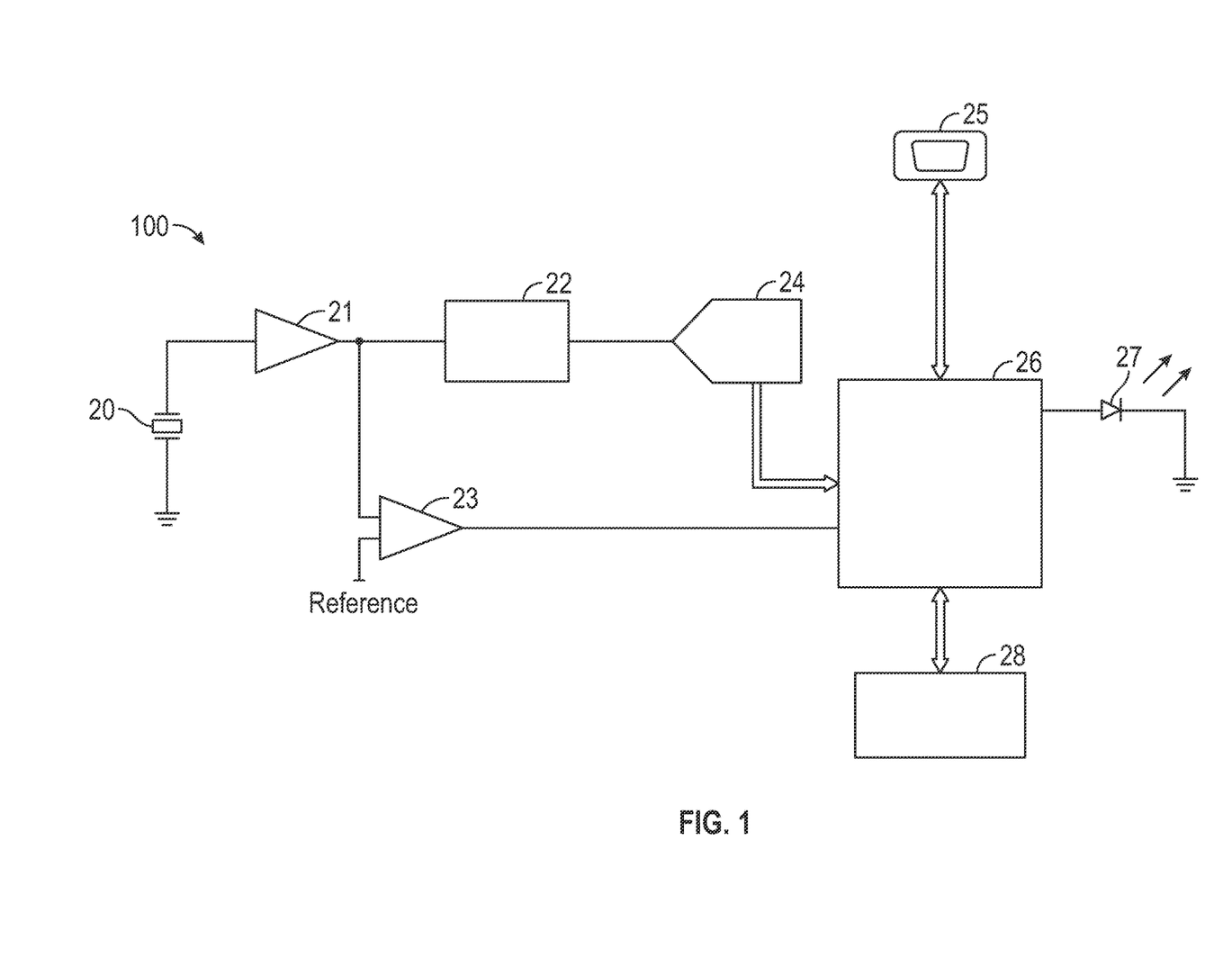
FIG. 1 illustrates a diagram of an exemplary system.

FIG. 1 illustrates an exemplary system 100 in accordance with one or more embodiments. The system 100 may be used to detect the existence of a pressure wave, which may be indicative of an event such as a blast, an explosion, etc.

The system 100 may include a sensor 20. The sensor 20 may include a magnetic coil or piezoelectric sensor that may generate an output based on an input (pressure) waveform. In some embodiments the sensor 20 may include a thermocouple that may provide an output based on a temperature of the input waveform. While discussed in terms of a sensor sensing a pressure waveform, it is understood that other waveforms from other types of events could be detected using other types of sensors in addition to or instead of pressure waves.

The output from the sensor 20 may be applied to a conditioning amplifier 21. The conditioning amplifier 21 may be used to amplify and/or filter the output of the sensor 20, but may not be needed in all aspects of the invention.

The output of the conditioning amplifier 21 may serve as a first input to a comparator 23. The comparator 23 may have a second input corresponding to a reference. The reference (e.g., the magnitude of the reference) may be selected in order to distinguish those events that are of interest (e.g., blasts, explosions, etc.) from those that are not (e.g., noise).

In the event that the first input to the comparator 23 exceeds the second input to the comparator 23, the output of the comparator 23 may be signaled to enable or power-on a recording circuit. As shown and described further below, a controller 26 may be included in the recording circuit and may receive the output of the comparator 23. Conversely, when the first input to the comparator 23 is less than the second input to the comparator 23, the output of the comparator 23 may be signaled to disable or power-off the recording circuit.

The recording circuit may include an analog to digital converter (ADC) 24, a controller 26, and a storage device 28. The storage device 28 may include a digital memory and/or a non-volatile memory, and may be connected to the controller 26 using wired and/or wireless connections. While shown as part of the recording circuit, it is understood that the storage device 28 could be removable from the recording circuit or contain removable media which allows the data to be read on another device (not shown). The controller 26 may include one or more processors. The recording circuit, when enabled or powered-on, may be configured to record samples of data (e.g., digital samples output by the ADC 24) associated with a pressure wave in the storage device 28.

The system 100 may include a communication port 25 and/or an indicator 27 (e.g., a light emitting diode or LED, a speaker to emit a sound, a tactile feedback mechanism or other mechanisms which convey information). The communication port 25 and/or the indicator 27 may be used to convey status information or data regarding an application that is the subject of the system 100. For example, if the system 100 is configured to detect an occurrence of an explosion, data or indication regarding the explosion (or a lack thereof) may be conveyed by the communication port 25 to be transmitted wired and/or wirelessly to a remote device, and/or the indicator 27 may provide an indication to an observer of the system 100 directly. However, it is understood that the port 25 and/or the indicator 27 need not be used in all aspects of the invention.

In some embodiments, the communication port 25 and/or the indicator 27 may be configured to provide a warning or indication when a battery (not shown) associated with the system 100 discharges, such that the remaining charge is in an amount that is less than a threshold. Such a warning may be used to schedule a maintenance activity (e.g., a battery replacement activity).

The system 100 may include a delay circuit 22. The delay circuit 22 may be configured to store data in analog form by utilizing a multi tap low power track and hold circuit, such as a bucket brigade circuit or the circuit 200 in FIG. 2. The number of taps associated with the circuit 22 may be selected to provide enough time for one or more components of the recording circuit (e.g., the ADC 24) to be enabled or powered-on prior to the data exiting the delay circuit 22. The delay circuit 22 may be configured to run at the conversion rate of the ADC 24.

Figure 2:
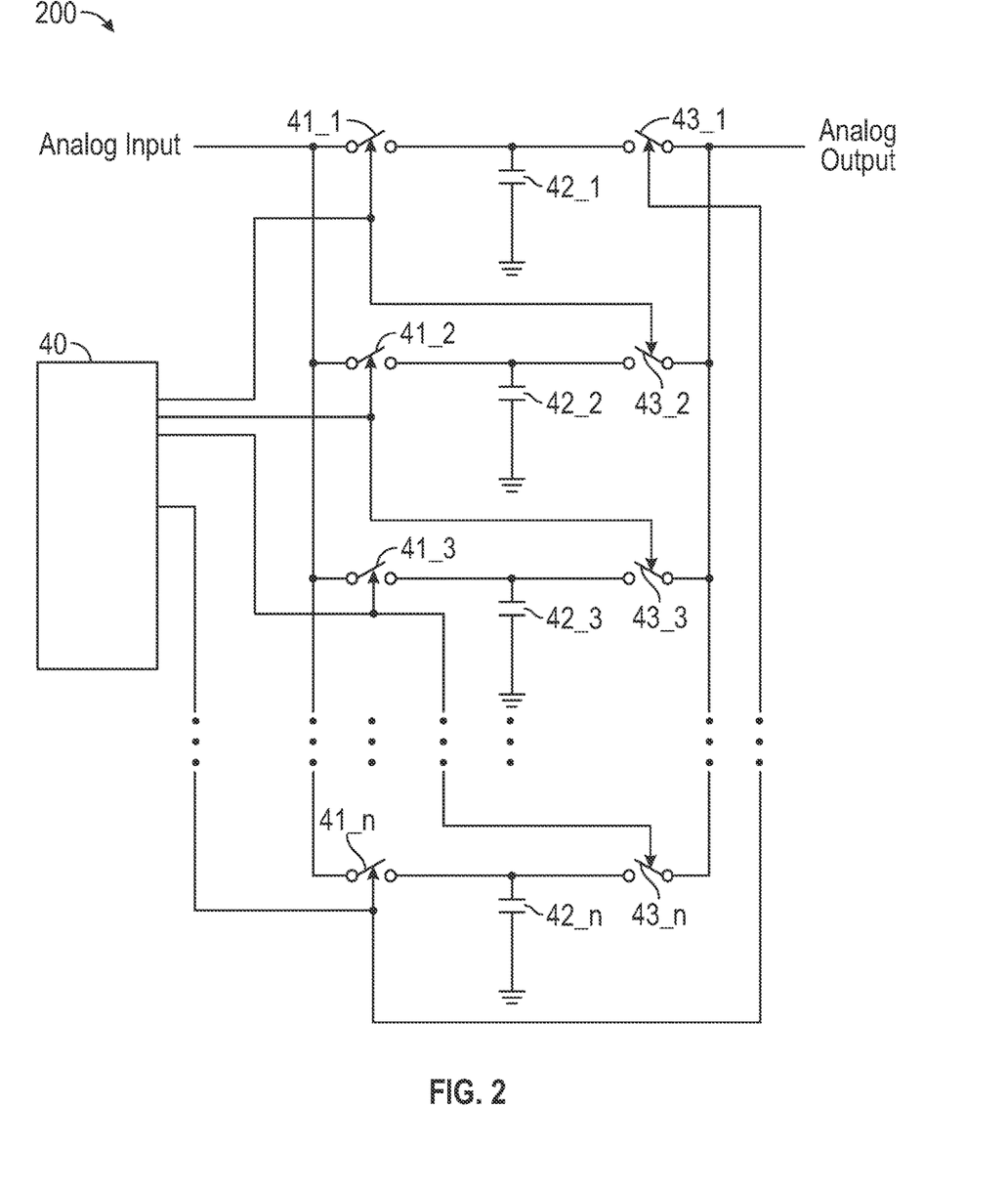
FIG. 2 illustrates a diagram of an exemplary circuit.

Referring to FIG. 2, a circuit 200 in accordance with one or more embodiments is shown. The circuit 200 may be implemented in connection with at least a portion of the system 100. For example, the circuit 200 may be associated with the circuit 22.

The circuit 200 may include an address generator 40. The address generator 40 may be configured to control the state of a number 'n' of switches, denoted as 41_1, 41_2, 41_3, . . . 41_n and 43_1, 43_2, 43_3, . . . 43_n in FIG. 2. The switches 41 and 43 may connect hold capacitors 42 (denoted as 42_1, 42_2, 42_3, . . . 42_n in FIG. 2) to analog input and output ports. The address generator 40 may control the state of the switches 41 and 43 such that the oldest data within the circuit 200 is connected to the analog output port. By way of example, in FIG. 2, the address generator 40 controls switch 41_1 to be closed concurrent with the switch 43_2 being closed with the remaining switches 41_2 through 41_n and 43_1, 43_3 through 43_n being open such that the capacitor 42_1 holds the most recent Analog Input while the oldest analog input is output from the capacitor 42_2 via the switch 43_2 as the Analog Output. In the next iteration or time instance, the address generator 40 may control switch 41_2 to be closed concurrent with the switch 43_3 being closed while commanding the remaining switches 41_1, 41_3 through 41_n, 43_1, 43_2, and 43_4 (not shown) through 43_n to be open.

As described above, the delay associated with the circuit 22 or the circuit 200 may be selected beyond the time required for a recording circuit to be enabled or powered-on. In doing so, it is possible to record a pressure waveform (e.g., a blast waveform) several samples prior to the signal reaching the trigger level associated with the reference of the comparator 23, thereby providing information or data regarding the rising edge of the pressure waveform.

As described above, the recording circuit may be powered-off when data of interest is not present (e.g., when the data is less than a threshold as established by the reference to the comparator 23). Power in a complementary metal oxide semiconductor (CMOS) circuit is proportional to the product of the equivalent circuit capacitance, a switching frequency, and an operating voltage. Removing power from unused circuits or components and disabling high speed clocks when data of interest is not present may greatly reduce the power consumption of an acquisition system (e.g., system 100). Incorporating a delay in a signal path provides time for returning or restoring full functionality while still preserving data that was acquired prior to a trigger condition.

In some embodiments, a delay may be implemented in discrete steps. The delay may correspond to one sampling period.

One or more components or devices of the system 100 and circuit 200 may be implemented using low voltage/low power CMOS multiplexers and supporting logic in conjunction with a low power clock running at a relatively low sampling frequency to minimize continuous power consumption.

In some embodiments, more than one channel or sensor circuit/system may be used. For example, four sensor circuits may be arranged orthogonally to aid in the determination of a pressure wave origin. Each of the sensor circuits may contain a delay circuit (e.g., circuit 22 and/or circuit 200) and a trigger circuit (e.g., comparator 23). Any delays associated with the channels may be synchronized. Therefore, analog to digital conversion can be performed sequentially without introducing a time skew between the channels. A trigger occurring on any of the channels may cause components of a recording circuit to be powered-on or enabled. Data obtained from the ADC 24 may be sequentially numbered and/or time stamped and stored in the storage device 28. Once the event has been recorded to the storage device 28, a sleep state may be re-entered with a high speed clocks stopped and unused circuitry powered-off or disabled. The sensor circuits or channels may be armed for the next trigger or event.

In embodiments where more than one sensor (e.g., sensor 20) is used, the recording circuit may be configured to store an identity of the sensor that causes the occurrence of the event to be detected by the trigger circuit.

Figure 3B:
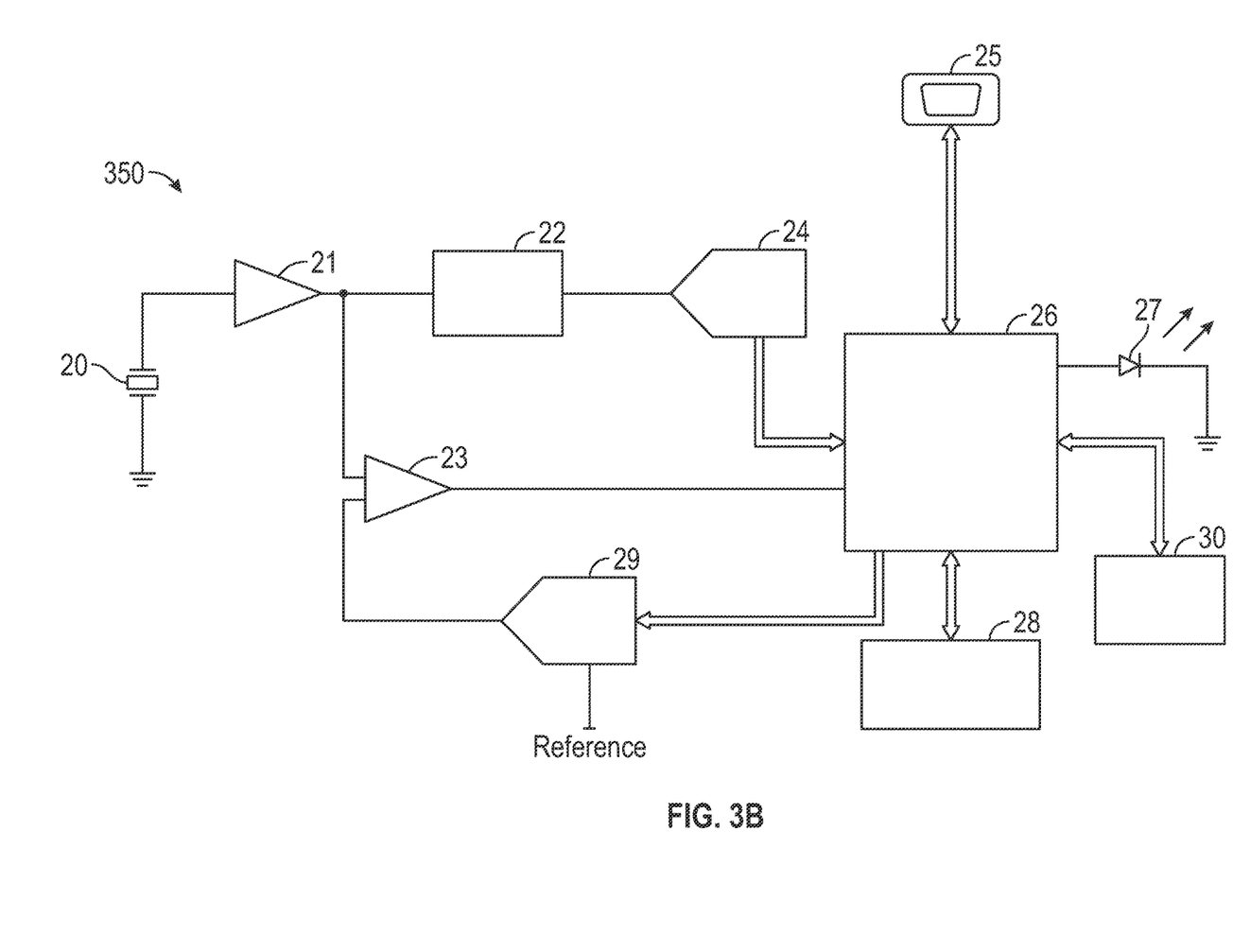
FIG. 3B illustrates a diagram of an exemplary circuit.

FIG. 3B illustrates a circuit 350 that may be used to provide a capability to adjust trip levels or reference thresholds as described above. The circuit 350 may include a digital to analog converter (DAC) 29 and/or a digital potentiometer 29, either or both of which can be used to provide an adjustable trip level as directed by the controller 26. In some embodiments, the controller 26 may contain, or be coupled to, a real time clock 30 or may communicate with a peripheral device 30 that maintains time and date information.

Figure 4:
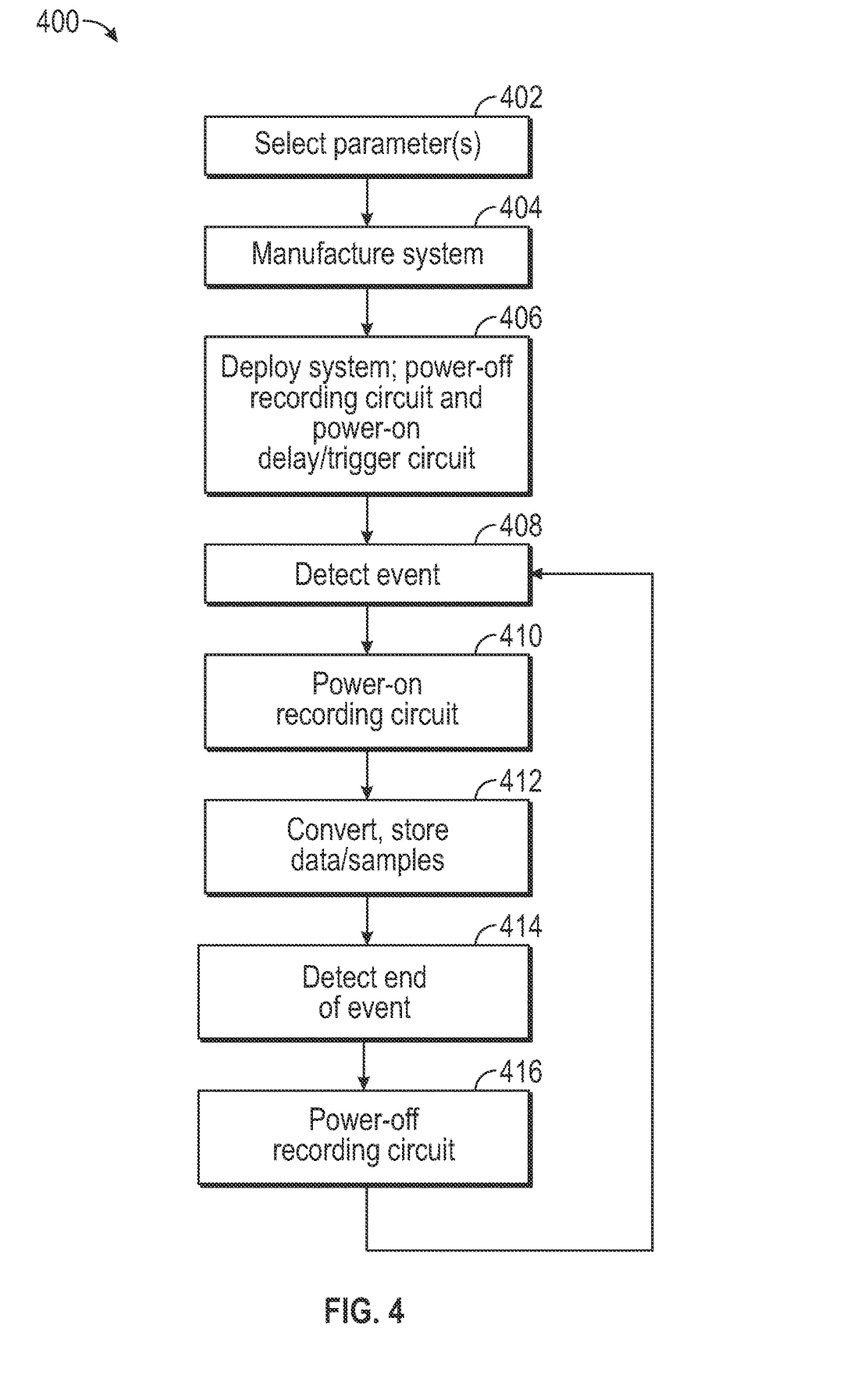
FIG. 4 illustrates a flow chart of an exemplary method.

Turning now to FIG. 4, a flow chart of an exemplary method 400 is shown. The method 400 may be executed by one or more systems, components, or devices, such as those described herein (e.g., the system 100). The method 400 may be used to minimize or reduce power consumption associated with data acquisition while still preserving an ability to capture data associated with, and leading up to, an event (e.g., an explosion).

In block 402, one or more parameters associated with a data acquisition system may be selected. The parameter selection may include a specification of one or more components of a recording circuit (e.g., one or more controllers, storage devices, ADCs, etc.). The parameter selection may include a specification of an application (e.g., mining, construction, etc.) or reference/threshold to use for that application. The parameter selection may include a number of delay components or type of delay circuit to use, potentially based on other parameter selections (e.g., the type of components used in the recording circuit).

In block 404, a system may be manufactured or fabricated in accordance with the parameters selected in block 402. Alternatively, a system may be configured in accordance with the parameters of block 402 after manufacture.

In block 406, the system may be deployed. As part of the deployment, a delay and/or triggering circuit may be enabled or powered-on, whereas a recording circuit may be disabled or powered-off. In this manner, data may be captured by the delay circuit leading up to an event that triggers the triggering circuit.

In block 408, the system may detect an event that exceeds a reference or threshold. For example, the triggering circuit may be triggered by the occurrence of the event, potentially in connection with one or more sensors and one or more references.

In block 410, the recording circuit may be enabled or powered-on based on the detected event of block 408.

In block 412, (sampled or track-and-hold) data associated with the detected event are read from the delay circuit (such as from capacitors 42 of the system 200 shown in FIG. 2), and are converted from an analog format to a digital format (such as in an ADC 24 of FIGS. 1 and 3B). The digital samples may be stored (such as in the storage 28 of FIGS. 1 and 3B). In some embodiments, the data or samples (e.g., digital samples) may be tagged or time-stamped as part of block 412.

In block 414, the end of the event may be detected.

In block 416, the recording circuit may be powered-off based on the detection of the end of the event in block 414. In this respect, a time delay may be imposed in transitioning from block 414 to block 416 to allow for all of the relevant data to have exited the delay circuit (e.g., delay circuit 22 and/or circuit 200), been converted, and stored. Alternatively, or additionally, the detection of the end of the event in block 414 may utilize a first reference or threshold than is different from a second reference or threshold used to detect the occurrence of the event in block 408. In some embodiments, recording of data and/or a powering-off of the recording circuit may terminate after a passage of a fixed amount of time or acquisition of a threshold number of samples associated with the event since the occurrence/detection of a trigger.

Flow may proceed from block 416 to block 408. The flow from block 416 to block 408 may be used to enable a rearming of the system after an event has been captured. In this respect, multiple events may be captured or recorded by the system.

The method 400 is illustrative. In some embodiments, one or more of the blocks or operations (or a portion thereof) may be optional. In some embodiments, the blocks or operations may execute in an order or sequence different from what is shown. In some embodiments, additional blocks or operations not shown may be included.

Embodiments of the disclosure may be used to reduce the power consumption of a waveform capturing monitor while maintaining the capability of capturing data points which occur prior to the pressure wave exceeding a predetermined magnitude. The use of multiple channels with different physical orientations may provide an indication of orientation relative to a blast origin. Data may be studied by medical professionals to correlate blast waveform signatures with personal injury. Data may be studied by forensic scientists to analyze structural damage to objects, such as vehicles and buildings. Extended battery life associated with a monitor may allow for a continuous monitoring without the need for frequent maintenance (e.g., battery replacement).

Aspects of the disclosure may be applied in connection with one or more applications. For example, aspects of the disclosure may be applied in connection with mining, construction, a bomb or explosive device application, a military application, a law enforcement application, and a firefighting application. Additionally, aspects could be used outside of explosive events, such as collisions or accidents such as occur in automobile accidents, sporting events, or other applications where data needs to be recorded while a recording device is being powered up. A reference or threshold may be selected for detecting an event based on the application.

As described herein, in some embodiments various functions or acts may take place at a given location and/or in connection with the operation of one or more apparatuses, systems, or devices. For example, in some embodiments, a portion of a given function or act may be performed at a first device or location, and the remainder of the function or act may be performed at one or more additional devices or locations.

Embodiments may be implemented using one or more technologies. In some embodiments, an apparatus or system may include one or more processors, and memory storing instructions that, when executed by the one or more processors, cause the apparatus or system to perform one or more methodological acts as described herein. Various mechanical components known to those of skill in the art may be used in some embodiments.

Embodiments may be implemented as one or more apparatuses, systems, and/or methods. In some embodiments, instructions may be stored on one or more computer-readable media, such as a transitory and/or non-transitory computer-readable medium. The instructions, when executed, may cause an entity (e.g., an apparatus or system) to perform one or more methodological acts as described herein.

Aspects of the disclosure have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps described in conjunction with the illustrative figures may be performed in other than the recited order, and that one or more steps illustrated may be optional.

The appendix attached hereto references one or more embodiments in accordance with one or more aspects of this disclosure.

APPENDIX

1. A method for capturing data associated with an occurrence of an event via a battery-powered recorder, comprising:
    storing analog data in a delay circuit while a recording circuit is powered off;
    detecting, by a trigger circuit, the occurrence of the event while the recording circuit is powered off;
    powering-on the recording circuit based on the detection of the event;
    converting samples of analog data associated with the event provided by the delay circuit to a digital format while the recording circuit powers on; and
    storing the converted digital samples after the recording circuit has powered on,
    wherein a time delay associated with the delay circuit is greater than a time it takes for the recording circuit to power-on.
2. The method of any preceding claim, wherein the delay circuit is configured as a multi tap track and hold circuit.
3. The method of any preceding claim, wherein the delay circuit runs at a conversion rate of an analog to digital converter (ADC) included in the recording circuit.

4. The method of any preceding claim, further comprising:
   detecting an end of the event; and
   powering-off the recording circuit based on the detection of the end of the event,
   wherein a second time delay is imposed between the detection of the end of the event and the powering-off of the recording circuit the second time, and wherein the second time delay is selected to enable digital samples associated with the event to be stored.
5. The method of any preceding claim, further comprising:
   synchronizing samples of analog data provided by sensor circuits.
6. The method of any preceding claim, further comprising:
   time-stamping the digital samples; and
   storing the time-stamps with the digital samples in a non-volatile memory of the recording circuit.
7. A system comprising:
   a trigger circuit to detect an occurrence of an event;
   a delay circuit to delay analog samples of data; and
   a recording circuit to store the delayed analog samples of data in a digital format when in a power-on state and to not store the delayed analog samples when in a power-off state,
   wherein a time delay associated with the delay circuit is greater than a time it takes for the recording circuit to power-on to the power-on state from the power-off state, and
   wherein the recording circuit is powered-on based on the detection of the occurrence of the event by the trigger circuit.
8. The system of claim 7, further comprising:
   at least one sensor comprising at least one of: a magnetic coil, a piezoelectric sensor, and a thermocouple, wherein an output of the at least one sensor is coupled to an input of the trigger circuit.
9. The system of claim 8, wherein the output of the at least one sensor is coupled to an input of a conditioning amplifier, and wherein an output of the conditioning amplifier is coupled to the input of the trigger circuit.
10. The system of any of claims 7 through 9, wherein the trigger circuit comprises a comparator, and wherein a reference is coupled to a first input of the comparator, and wherein the reference is selected to distinguish between the occurrence and the non-occurrence of the event and wherein the reference is selected based on a programmable level setting device.
11. The system of claim 10, wherein the reference is selected based on an application associated with the event.
12. The system of any of claims 7 through 11, further comprising a battery which powers the recording circuit.
13. The system of claim 12, further comprising:
    at least one of an indicator and a communication port configured to convey a status regarding at least one of the event, the data, the digital samples, and an indication that the battery associated with the system is charged to an amount that is less than a threshold.
14. The system of any of claims 7 through 13, wherein the recording circuit is configured to be powered-off after a second time delay based on a detection of the end of the occurrence of the event by the trigger circuit.
15. The system of any of claims 7 through 14, wherein:
    the delay circuit comprises:
      an analog input port;
      an analog output port coupled to an input of the recording circuit;
      hold capacitors to hold analog samples from the analog input port;
      a plurality of input switches selectively connecting the analog input port to the hold capacitors;
      a plurality of output switches selectively connecting the analog output port to the hold capacitors; and
      an address generator configured to control the plurality of input switches coupling the hold capacitors to the input analog port and the plurality of output switches coupling the hold capacitors and the output analog port, and
    the address generator connects the oldest analog sample present in the delay circuit to the output analog port.

What is claimed is:
1. A system comprising:
   a trigger circuit to detect an occurrence of an event;
   a delay circuit to delay analog samples of data, wherein the data is associated with a pressure waveform generated by the event; and
   a recording circuit to store the delayed analog samples of data in a digital format when in a power-on state and to not store the delayed analog samples when in a power-off state,
   wherein a time delay associated with the delay circuit is greater than a time it takes for the recording circuit to power-on to the power-on state from the power-off state,
   wherein the recording circuit is powered-on based on the detection of the occurrence of the event by the trigger circuit, and
   wherein the delayed analog samples of data are converted to a digital format while the recording circuit powers on from the power-off state to the power-on state.
2. The system of claim 1, further comprising:
   at least one sensor,
   wherein an output of the at least one sensor is coupled to an input of the trigger circuit.
3. The system of claim 2, wherein the at least one sensor comprises at least one of: a magnetic coil, a piezoelectric sensor, and a thermocouple.
4. The system of claim 2, wherein the output of the at least one sensor is coupled to an input of a conditioning amplifier, and wherein an output of the conditioning amplifier is coupled to the input of the trigger circuit.
5. The system of claim 1, wherein the trigger circuit comprises a comparator, and wherein a reference is coupled to a first input of the comparator, and wherein the reference is selected to distinguish between the occurrence and the non-occurrence of the event.
6. The system of claim 5, wherein the reference is selected based on at least one of: a reference divider network and a programmable level setting device.
7. The system of claim 5, wherein the reference is selected based on an application associated with the event.
8. The system of claim 7, further comprising a battery which powers the recording circuit.
9. The system of claim 1, further comprising:
   at least one of an indicator and a communication port configured to convey a status regarding at least one of the event, the data, and the digital samples.
10. The system of claim 1, further comprising:
    a battery which powers the recording circuit, and
    at least one of an indicator and a communication port configured to provide an indication that the battery associated with the system is charged to an amount that is less than a threshold.

11. The system of claim 1, wherein the recording circuit is configured to be powered-off after a second time delay based on a detection of the end of the occurrence of the event by the trigger circuit.

12. The system of claim 1, wherein:
the delay circuit comprises:
an analog input port;
an analog output port coupled to an input of the recording circuit;
hold capacitors to hold analog samples from the analog input port;
a plurality of input switches selectively connecting the analog input port to the hold capacitors;
a plurality of output switches selectively connecting the analog output port to the hold capacitors; and
an address generator configured to control the plurality of input switches coupling the hold capacitors to the analog input port and the plurality of output switches coupling the hold capacitors and the output analog port, and
the address generator connects an oldest analog sample present in the delay circuit to the output analog port.

13. A system comprising:
a trigger circuit to detect an occurrence of an event;
a delay circuit to delay analog samples of data; and
a recording circuit to store the delayed analog samples of data in a digital format when in a power-on state and to not store the delayed analog samples when in a power-off state,
wherein a time delay associated with the delay circuit is greater than a time it takes for the recording circuit to power-on to the power-on state from the power-off state,
wherein the recording circuit is powered-on based on the detection of the occurrence of the event by the trigger circuit, and
wherein the delayed analog samples of data are converted to a digital format while the recording circuit powers on from the power-off state to the power-on state.

14. The system of claim 13, wherein the delay circuit operates at a conversion rate equal to a conversion rate of an analog-to-digital converter that converts the analog samples of data to the digital format.

* * * * *